United States Patent [19]
Huby et al.

[11] Patent Number: 6,054,556
[45] Date of Patent: Apr. 25, 2000

[54] MELANOCORTIN RECEPTOR ANTAGONISTS AND AGONISTS

[75] Inventors: Victor J. Huby, Tucson, Ariz.; Sejin Lim, Kuung-Gi Do, Rep. of Korea; Wei Yuan, Sommerville, Mass.

[73] Assignee: The Arizona Board of Regents on Behalf of the University of Arizona, Tucson, Ariz.

[21] Appl. No.: 08/980,238

[22] Filed: Nov. 28, 1997

Related U.S. Application Data

[63] Continuation-in-part of application No. 08/420,972, Apr. 10, 1995, Pat. No. 5,731,408.

[51] Int. Cl.[7] .................................................... C07K 5/00
[52] U.S. Cl. ........................... 530/317; 530/312; 930/270
[58] Field of Search ..................................... 530/317, 312; 930/270

[56] References Cited

U.S. PATENT DOCUMENTS 5,731,408  3/1998  Hadley et al. ......................... 530/317

OTHER PUBLICATIONS

Degrado, W., Advances in Protein Chemistry, vol. 39, pp. 51–124 (see page 60), 1988.

*Primary Examiner*—Michael P. Woodward
*Assistant Examiner*—C. Delacroix-Muirheid
*Attorney, Agent, or Firm*—Yahwak & Associates

[57] ABSTRACT

Cyclic lactam peptides are disclosed which inhibit at various levels of antagonism the melanocortin 1 receptor (MC1R), melanocortin 3 receptor (MC3R), melanocortin 4 receptor (MC4R), and Melanocortin 4 receptor (MC5R).

17 Claims, No Drawings

MELANOCORTIN RECEPTOR ANTAGONISTS AND AGONISTS

This is a Continuation-in-Part of earlier-filed U.S. patent application Ser. No. 08/420,972 filed Apr. 10, 1995 which is now U.S. Pat. No. 5,731,408.

Research that led to the making of the present invention was supported, in part, by funds from the United States Public Health Service. Accordingly, the United States Government has certain statutory rights to the invention described herein under 35 USC 200 et seq.

BACKGROUND OF THE INVENTION

While pharmacological methods have been traditionally used to define receptor types and subtypes, receptor cloning experiments have often led to the discovery of novel receptor types and subtypes within many receptor families. Following the cloning of the melanocyte stimulating hormone (MSH) gene [see Science 257:543 (1992)] and the adrenocorticotropic hormone (ACTH) receptor gene [see FEBS Lett. 309:417 (1992)], for example, three unique yet related genes were identified that also encoded functional, high affinity receptors for the MSH and ACTH peptides [see PNAS USA 90:8856 (1993); J. Biol. Chem. 268:8246 (1993); J. Biol. Chem. 268:15174 (1993);

Biochem. Biophys. Res. Comm. 200:1214 (1994); Biochem. Biophys. Res. Comm. 195:866 (1993); Biochem. J. 299:367 (1994); Biochem. 33:4543 (1994); Mol. Endo. 8:1298 (1994); J. Mol. Endochrinol. 12:203 (1994); and Biochem. Biophys.

Res. Comm. 200:1007 (1994)]. Named by number in the order of their discovery, the melanocortin-1 receptor gene has been found thus far to be expressed primarily in the epidermal tissues; melanocortin-3, melanocortin-4, and melanocortin-5 receptor genes have been found thus far to be expressed primarily in the hypothalamus, mid-brain and brainstem (MC3-R, and MC4-R), or in a wide distribution of peripheral tissues (MC5-R).

The melanocortin peptides have been reported to have a wide variety of biological activities outside of their effects upon pigmentation and steroidogenesis, known to be mediated by the MSH and ACTH receptors. However, given the complexity of possible sites of expression of the MC3, MC4 and MC5 receptors, it has not been possible to unambiguously identify any simple correlation between these receptors and the reported biological activities of their ligands. Consequently, potent and specific agonists and antagonists would be extremely valuable tools for determining the physiological roles of the MC3, MC4 and MC5 receptors; the roles of the MC1 (pigment cell receptor) and MC2 (primary receptor for ACTH in the adrenal gland) receptors are fairly well-documented.

While prior structure-function analyses have been reported in the past on the affinity and potency of the α-MSH peptide at the MSH receptor site [for reviews see Peptide Protein Rev. 3:1 (1984), The Melanotropic Peptides, Vol. I, II, and III (CRC Press) (1988)], only a few relatively weak antagonists have resulted from these studies [see Int. J. Peptide Protein Res. 35:228 (1990); Peptides 11:351 (1990); and Peptide Res 3:140 (1989)].

Accordingly there is still a need to provide for potent and specific antagonists that will allow for the determination of the physiological roles of these melanocortin receptors.

SUMMARY OF THE INVENTION

It is, therefore, a primary aspect of the present invention to describe the discovery of melanocortin analogues that can inhibit at various levels of antagonism, the malanocortin 1 receptor, melanocortin 3 receptor, melanocortin 4 receptor, and melanocortin 5 receptor.

More specifically, the present description describes a family of antagonists for the MC1, MC3 and MC4 and MC5 receptors that are heptapeptides having the cyclic peptide structures:

| Compound No. | Amino Acid Sequence |
|---|---|
| 1 | Ac-Nle-c[Asp-Trp-D-Nal(2')-Arg-Nal(2')-Lys]-NH$_2$; |
| 2 | Ac-Nle-c[Asp-His(1-Me)-D-Nal(2')-Arg-Trp-Lys]-NH$_2$; |
| 3 | Ac-Nle-c[Asp-His(3-Me)-D-Nal(2')-Arg-Trp-Lys]-NH$_2$; |
| 4 | Ac-Nle-c[Asp-Tal(4')-D-Nal(2')-Arg-Trp-Lys]-NH$_2$; |
| 5 | Ac-Nle-c[Asp-His(1-Me)-D-Nal(2')-Arg-Nal(2')-Lys]-NH$_2$; |
| 6 | Ac-Nle-c[Asp-His(3-Me)-D-Nal(2')-Arg-Nal(2')-Lys]-NH$_2$; |
| 7 | Ac-Nle-c[Asp-Tal(4')-D-Nal(2')-Arg-Nal(2')-Lys]-NH$_2$; |
| 8 | Ac-Nle-c[Asp-His-(2R,3R)-β-MeNal(2')-Arg-Trp-Lys]-NH$_2$; |
| 9 | Ac-Nle-c[Asp-His-(2R,3S)-β-MeNal(2')-Arg-Trp-Lys]-NH$_2$; |
| 10 | Ac-Nle-c[Asp-Trp-D-Phe-Arg-Nal(2')-Lys]-NH$_2$; |
| 11 | Ac-Nle-c[Asp-His-D-Nal(2')-Arg-Nal(2')-Lys]-NH$_2$; |
| 12 | Ac-Nle-c[Asp-His-Nal(2')-Arg-Trp-Lys]-NH$_2$; |
| 13 | Ac-Nle-c[Asp-His-D-Nal(2')-Nle-Trp-Lys]-NH$_2$; |
| 14 | Ac-Nle-c[Asp-Trp-D-Nal(2')-Nle-Trp-Lys]-NH$_2$; |
| 15 | Ac-Nle-c[Asp-His-D-Phe-Nal(2')-Trp-Lys]-NH$_2$; |
| 16 | Ac-Nle-c[Asp-His-D-Nal(2')-Arg-D-Nal(2')-Lys]-NH$_2$; |

This and other aspects of the present invention will become clearer in the following discussion and description, both provided for purposes of clarification and not limitation as to the scope of the present invention.

DETAILED DESCRIPTION OF THE INVENTION

In the following description, the abbreviations used for amino acids, protecting groups and peptides follow the recommendations of the IUPAC-IUB Commission on Biochemical Nomenclature as described in J. Biol. Chem. 250:3215 (1975); all optically active amino acids are of the L variety unless otherwise specified (since each of the peptides described herein contain an internal cyclic bridge or bond, i.e., the designation "c[.....] refers to the cyclic nature of the peptides, i.e., indicating that a bond or bridge exists between the first and last amino acids in the bracketed series, the resulting peptides are considered to be cyclic amino acid-containing peptides). Other abbreviations used throughout this description include "Nal" indicating naphthylalanine, "nM" indicating nanomolar, "pM" indicating picomolar, Nle indicating norleucine, OFm indicating fluorenylmethyloxy, Fmoc indicating fluorenylmethyloxycarbonyl, MC indicating melanocortin; and MC-R indicating melanocortin receptor. In addition, the structural amino acids designated in the above table of amino acid sequences include:

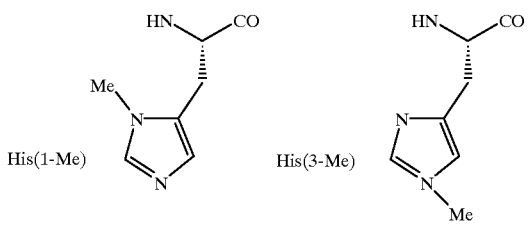

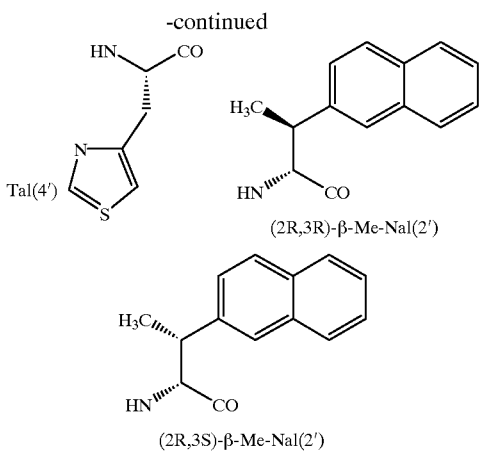

(2R,3R)-β-Me-Nal(2')

(2R,3S)-β-Me-Nal(2')

The peptides described herein may be synthesized by well-known methods as, for example, the solid-phase methods of peptide synthesis [see J. Med. Chem. 30:2126 (1987] on a p-methylbenzhydrylamine resin (substitution 0.34 meq amine/g resin) using a VEGA 250 semi-automated peptide synthesizer as described in U.S. Pat. Nos. 5,731,408 (which is the parent to this Continuation-in-Part patent application) 5,674,839, 5,683,981, or as described in Reaction Polymers 22:231 (1994), the disclosures of which are all incorporated in toto herein. For example, using the synthesis protocol in Reaction Polymers, supra, Compund 1, i.e., Ac-Nle-c[Asp-Trp-D-Nal(2')-Arg-Nal(2')-Lys]-NH$_2$, may be prepared according to the following Example I:

EXAMPLE I

The peptide Ac-Nle-c[Asp-Trp-D-Nal(2')-Arg-Nal(2')-Lys]-NH$_2$ was synthesized on a p-methylbenxhydrylamine (pMBHA) resin (0.35 meq amine/gram resin) using a Milligen/Biosearch 9500 Peptide Synthesizer. A four-fold excess of appropriate N$^\alpha$-BOC-protected amino acid was used at each coupling step. Couplings were performed by using diisopropylcarbondiimidide-hydroxybenxotriaxole (DIC-HOBT) as the coupling agent. A mixture of trifluoroacetic acid-dichloromethane-anisole (TFA-DCM-anisole, 50:48:2) was used to deblock the N$^\alpha$-BOC group after each coupling step. Neutralization was accomplished lusing Diisopropylethylamine in dichloromethane. In this manner, the following fully-protected peptide-resin corresponding to the desired peptide was synthesized: N$^\alpha$-BOC-Asp(OFm)-Trp(Formyl)-D-Nal(2')-Arg(Tosyl)-Nal(2')-Lys-(Fmoc)-Resin. The N$^\alpha$-Fmoc group from Lys and β-OFm from Asp were cleaved simultaneously by the treatement of the peptide resin with 20% piperidine in N,N-Dimethylformamide for 1 hour. The resulting ε-NH$_2$ and β-COOH side chain functional groups on the peptide resin N$^\alpha$-Boc-Asp-Trp-D-Nal(2')-Arg(Tosyl)-Nal(2')-Lys-Resin were condensed together using benxotrixole-1-yl-oxy-tris-(dimethylamino)-phosphonium hexafluorophosphate (BOP) reagent (at a 6-fold excess) in N methyl pyrrolidone (NMP) and in the presence of 8 8 molar excess of diisopropylethylamine (DIEA) as described previously in the literature (Reactive Polymers, supra). The cyclization process was monitored by the Kaiser test [see Anal. Biochem. 34:595 (1970)] and was usually completed in 2 to 6 hours. The N$^\alpha$-Boc group was cleaved and the N$^\alpha$-Boc-Nle group was coupled to the N-terminus using DIC-HOBT methodology.

After removal of the N$^\alpha$-Boc group, the N-terminus amino group was acetylated using acetyl anhydride. The dried peptide resin was next treated with HF in the presence of 10% anisole at 0° C. for 1 hour. The crude peptide was then purified by HPLC and characterized by mass spectrometry (ESI) and amino acid analysis.

EXAMPLE II

Bioassays were performed on frog (Rana pipiens) skin according to published protocols [see J. Med. Chem. 30:2126 (1987) and Gen. Comp. Endocrinol. 55:104 (1984)]. Briefly, in these assays the darkening of skin due to dispersion of melanin granules within the melanocytes in response to the melanotropin peptides according to the present invention is measured by photoreflectance methods. The agonist potency of each peptide was determined from the dose response curves comparing the skin darkening with that produced by the native hormone, α-MSH. Prolongation of the biological response was measured by continued monitoring of the melanosome dispersion for up to 3 hours following removal of the peptide in the bathing solution through washing of the skins. The antagonistic activity profile was measured by pre-incubating the skins for 1 hour in various concentrations of the antagonist. After pre-incubation, a known concentration of α-MSH was added and its melanotropic activity determined. Dose-response curves generated for α-MSH in this manner were used to determine the pA$_2$ values (representing the -log10 of the average molar concentration of the antagonist that will reduce the response of α-MSH (agonist) from 2X units to X units) [see Br. J. Pharmacol. 2:189 (1947)].

In addition to the classical frog skin assay conducted in accordance with this example, additional assays for agonist and antagonistic activity were performed.

EXAMPLE III

The peptides according to the present invention were assayed for agonist and antagonist activity using cloned hMC1, mMC1-R, hMC3-R, hMC4-R and mMC5-R transfected into the stable cell line Clonal 293. Transduction was measured by its affect on cAMP production using the following method.

Clonal 293 cell lines expressing the human MSH receptor, human MC3-R, human MC4-R, and mouse MC5-R were transfected with a pCRE/β-galactosidase construct using a CaPO$_4$ method [see Mol. Cell. Biol. 7:2745 (1987)]. 4 μg of pCRE/β-galactosidase DNA was used for transfection of a 10 cm dish of cells. After 15 to 24 hours post-transfection, cells were split into 96-well plates with 20,000 to 30,000 cells per well, and incubated at 37° C. in a 5% CO$_2$ incubator until 48 hours post-transfection. Cells were then stimulated with different peptides diluted in stimulation medium (Dulbecco's modified Eagle's medium containing 0.1 mg/ml bovine serum albumin and 0.1 mM isobutylmethylxanthine) for 6 hours. Agonist activity was measured by stimulating cells with various concentrations of peptide, and antagonist activity was measured by stimulating MC3 and MC4 receptor cell lines with various concentrations of peptide. After stimulation, cells were lysed in 50 μl lysis buffer (250 mM Tris-HCl, pH 8.0, 0.1% Triton X-100), frozen and thawed, and then assayed for b-galactosidase activity.

The results for biological activity of the cyclic peptides according to the present invention in frog skin (Example 11) and different receptor sites (Example III) are tabulated below:

| \multicolumn{5}{c}{BIOLOGICAL ACTIVITIES OF CYCLIC MELANOTROPIN ANALOGUES AT DIFFERENT RECEPTORS} |

| Compound | Frog Skin | hMC3-R | hMC4-R | mMC5-R |
|---|---|---|---|---|
| 1 | Antagonist, Irreversible 10-6-10-8 M — no Agonism | Antagonist nM range | Antagonist nM range | Full Antagonist pM range |
| 2 | Antagonist, Irreversible 10-6-10-8 M — no Agonism | Antagonist nM range | Antagonist nM range | Full Antagonist pM range |
| 3 | Antagonist, Irreversible 10-6-10-8 M — no Agonism | Antagonist nM range | Antagonist nM range | Full Antagonist pM range |
| 4 | Antagonist, Irreversible 10-6-10-8 M — no Agonism | Antagonist nM range | Antagonist nM range | Full Antagonist pM range |
| 5 | Antagonist, Irreversible 10-6-10-8 M — no Agonism | Antagonist nM range | Antagonist nM range | Full Antagonist pM range |
| 6 | Antagonist, Irreversible 10-6-10-8 M — no Agonism | Antagonist nM range | Antagonist nM range | Full Antagonist pM range |
| 7 | Antagonist, Irreversible 10-6-10-8 M — no Agonism | Antagonist nM range | Antagonist nM range | Full Antagonist pM range |
| 8 | Antagonist, $\mu$M range, 10-6-10-7 M — no Agonism | NT | NT | NT |
| 9 | Antagonist, $\mu$M range 10-6-10-7 | NT | NT | NT |
| 10 | Full Agonist | Agonist | Agonist | Agonist |
| 11 | Antagonist — Partial Agonist | Antagonist $\mu$M–nM range | Antagonist $\mu$M–nM range | Partial Agonist/Antagonist |
| 12 | Agonist | Agonist | Agonist | Partial Agonist/Antagonist |
| 13 | Agonist | Partial Agonist/Antagonist | Partial Agonist/Antagonist | Agonist |
| 14 | Antagonist 10-6M — no Agonism | Weak Antagonist | Partial Agonist/Antagonist | Agonist |
| 15 | Agonism | NT | NT | NT |
| 16 | Agonism | Antagonist $\mu$M–nM range | Antagonist $\mu$M–nM range | Partial Agonist/Antagonist |

As shown in Table I, peptides 1–7 was a potent antagonist in all four test systems (frog skin, and the cloned hMC3, hMC4, and mHC5 receptors); peptide 10 was a potent agonist in all four test systems; while the other peptides shared agonist and antagonist propertied in at least one of the test systems (Peptides 8, 9 and 15 have been evaluated in only a single test system, frog skin, at the present time).

In addition to the biological activity of the peptides according to the present invention as potent and specific agonists and antagonists (thereby making them an extremely valuable research tool for determining the physiological roles of the MC1, MC3, MC4 and MC5 receptors), these peptides may also be used to block the normal physiological response of cells to natural melanotropin (e.g., α-MSH). For example, some researchers have suggested that melanoma tumor cells secrete α-MSH which then results in a proliferation of these cells. If so, an antagonist such as the peptides according to the present invention may help delay melanoma growth and metastases; if a melanotropin is known to cause a physical or biochemical response in man, an antagonist may block such a response. Considering the present level of understanding on both peripheral and CNS receptors, some of the potential uses of the antagonists according to the present invention may be to block the proposed autocrine and/or paracrine actions of α-MSH in the proliferation of melanoma tumors; as a vector to direct therapeutic ligands at the site of specific classes of MSH receptors; and the structural features of the peptides according to the present invention suggest that they may have facile passage across the blood-brain barrier and as such these antagonists may find extensive uses as intervention agents in various physiological processes mediated in the brain or in the periphery by MSH such as, for example, learning and memory processes, sexual behavior, regulation of body temperature, immune response, and as a vehicle for drugs that may otherwise not cross the blood-brain barrier. Unfortunately, until such uses of the peptides can be confirmed, their uses are presently limited primarily as valuable research, screening and standard reagents for studying potential pharmaceutically active molecules, and as extremely valuable research tools for determining the physiological roles of the MC1, MC3, MC4 and MC5 receptors.

Having thus described our invention and the manner and process of making and using it in such full, clear, concise and exact terms so as to enable any person skilled in the art to which it pertains, or with which it is most nearly connected, to make and use the same;

We claim:
1. A cyclic peptide selected from the group consisting of:
Ac-Nle-c[Asp-Trp-D-Nal(2')-Arg-Nal(2')-Lys]-NH$_2$ (SEQ ID NO: 1);
Ac-Nle-c[Asp-His(1-Me)-D-Nal(2')-Arg-Trp-Lys]-NH$_2$ (SEQ ID NO: 2);
Ac-Nle-c[Asp-His(3-Me)-D-Nal(2')-Arg-Trp-Lys]-NH$_2$ (SEQ ID NO: 3);
Ac-Nle-c[Asp-Tal(4')-D-Nal(2')-Arg-Trp-Lys]-NH$_2$ (SEQ ID NO: 4);
Ac-Nle-c[Asp-His(1-Me)-D-Nal(2')-Arg-Nal(2')-Lys]-NH$_2$ (SEQ ID NO: 5);
Ac-Nle-c[Asp-His(3-Me)-D-Nal(2')-Arg-Nal(2')-Lys]-NH$_2$ (SEQ ID NO: 6);
Ac-Nle-c[Asp-Tal(4')-D-Nal(2')-Arg-Nal(2')-Lys]-NH$_2$ (SEQ ID NO: 7);
Ac-Nle-c[Asp-His-(2R,3R)-β-MeNal(2')-Arg-Trp-Lys]-NH$_2$ (SEQ ID NO: 8);
Ac-Nle-c[Asp-His-(2R,3S)-β-MeNal(2')-Arg-Trp-Lys]-NH$_2$ (SEQ ID NO: 9);
Ac-Nle-c[Asp-Trp-D-Phe-Arg-Nal(2')-Lys]-NH$_2$ (SEQ ID NO: 10);
Ac-Nle-c[Asp-His-D-Nal(2')-Arg-Nal(2')-Lys]-NH$_2$ (SEQ ID NO: 11);
Ac-Nle-c[Asp-His-Nal(2')-Arg-Trp-Lys]-NH$_2$ (SEQ ID NO: 12);
Ac-Nle-c[Asp-His-D-Nal(2')-Nle-Trp-Lys]-NH$_2$ (SEQ ID NO: 13);
Ac-Nle-c[Asp-Trp-D-Nal(2')-Nle-Trp-Lys]-NH$_2$ (SEQ ID NO: 14);
Ac-Nle-c[Asp-His-D-Phe-Nal(2')-Trp-Lys]-NH$_2$ (SEQ ID NO: 15); and
Ac-Nle-c[Asp-His-D-Nal(2')-Arg-D-Nal(2')-Lys]-NH$_2$ (SEQ ID NO: 16).
2. The peptide according to claim 1 which is:
Ac-Nle-c[Asp-Trp-D-Nal(2')-Arg-Nal(2')-Lys]-NH$_2$ (SEQ ID NO: 1).
3. The peptide according to claim 1 which is:
Ac-Nle-c[Asp-His(1-Me)-D-Nal(2')-Arg-Trp-Lys]-NH$_2$ (SEQ ID NO: 2).
4. The peptide according to claim 1 which is:
Ac-Nle-c[Asp-His(3-Me)-D-Nal(2')-Arg-Trp-Lys]-NH$_2$ (SEQ ID NO: 3).
5. The peptide according to claim 1 which is:
Ac-Nle-c[Asp-Tal(4')-D-Nal(2')-Arg-Trp-Lys]-NH$_2$ (SEQ ID NO: 4).
6. The peptide according to claim 1 which is:
Ac-Nle-c[Asp-His(1-Me)-D-Nal(2')-Arg-Nal(2')-Lys]-NH$_2$ (SEQ ID NO: 5).
7. The peptide according to claim 1 which is:
Ac-Nle-c[Asp-His(3-Me)-D-Nal(2')-Arg-Nal(2')-Lys]-NH$_2$ (SEQ ID NO: 6).
8. The peptide according to claim 1 which is:
Ac-Nle-c[Asp-Tal(4')-D-Nal(2')-Arg-Nal(2')-Lys]-NH$_2$ (SEQ ID NO: 7).
9. The peptide according to claim 1 which is:
Ac-Nle-c[Asp-His-(2R,3R)-β-MeNal(2')-Arg-Trp-Lys]-NH$_2$ (SEQ ID NO: 8).
10. The peptide according to claim 1 which is:
Ac-Nle-c[Asp-His-(2R,3S)-β-MeNal(2')-Arg-Trp-Lys]-NH$_2$ (SEQ ID NO: 9).
11. The peptide according to claim 1 which is:
Ac-Nle-c[Asp-Trp-D-Phe-Arg-Nal(2')-Lys]-NH$_2$ (SEQ ID NO: 10).
12. The peptide according to claim 1 which is:
Ac-Nle-c[Asp-His-D-Nal(2')-Arg-Nal(2')-Lys]-NH$_2$ (SEQ ID NO: 11).
13. The peptide according to claim 1 which is:
Ac-Nle-c[Asp-His-Nal(2')-Arg-Trp-Lys]-NH$_2$ (SEQ ID NO: 12).
14. The peptide according to claim 1 which is:
Ac-Nle-c[Asp-His-D-Nal(2')-Nle-Trp-Lys]-NH$_2$ (SEQ ID NO: 13).
15. The peptide according to claim 1 which is:

Ac-Nle-c[Asp-Trp-D-Nal(2')-Nle-Trp-Lys]-NH$_2$ (SEQ ID NO: 14).

16. The peptide according to claim 1 which is:

Ac-Nle-c[Asp-His-D-Phe-Nal(2')-Trp-Lys]-NH$_2$ (SEQ ID NO: 15).

17. The peptide according to claim 1 which is:

Ac-Nle-c[Asp-His-D-Nal(2')-Arg-D-Nal(2')-Lys]-NH$_2$ (SEQ ID NO: 16).

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 7 amino acids
       (B) TYPE:amino acid
       (C) STRANDEDNESS:single
       (D) TOPOLOGY:cyclic (ii) MOLECULE TYPE:peptide (ix) FEATURE:
       (D) OTHER INFORMATION: Position 1 is Norleucine; position
           4 is D-Naphthylalanine; position 6 is L-naphthylalanine;
           peptide is cyclic between positions 2 and 7

(xi) SEQUENCE DESCRIPTION: SEQ ID NO:1:

Xaa Asp Trp Xaa Arg Xaa Lys
              5

(2) INFORMATION FOR SEQ ID NO:2:

(i) SEQUENCE CHARACTERISTICS:
       (A) LENGTH: 7 amino acids
       (B) TYPE:amino acid
       (C) STRANDEDNESS:single
       (D) TOPOLOGY:cyclic (ii) MOLECULE TYPE:peptide (ix) FEATURE:
       (D) OTHER INFORMATION: Position 1 is Norleucine; position
           3 is 1-Me Histidine; position 4 is D-Naphthylalanine;
           peptide is cyclic between positions 2 and 7

(xi) SEQUENCE DESCRIPTION: SEQ ID NO:2:

Xaa Asp Xaa Xaa Arg Trp Lys
              5

(2) INFORMATION FOR SEQ ID NO:3:

(i) SEQUENCE CHARACTERISTICS:
       (A) LENGTH: 7 amino acids
       (B) TYPE:amino acid
       (C) STRANDEDNESS:single
       (D) TOPOLOGY:cyclic (ii) MOLECULE TYPE:peptide (ix) FEATURE:
       (D) OTHER INFORMATION: Position 1 is Norleucine; position
           3 is 3-Me Histidine; position 4 is D-Naphthylalanine;
           peptide is cyclic between positions 2 and 7

(xi) SEQUENCE DESCRIPTION: SEQ ID NO:3:

Xaa Asp Xaa Xaa Arg Trp Lys
              5

(2) INFORMATION FOR SEQ ID NO:4:

(i) SEQUENCE CHARACTERISTICS:
       (A) LENGTH: 7 amino acids
       (B) TYPE:amino acid
       (C) STRANDEDNESS:single
       (D) TOPOLOGY:cyclic (ii) MOLECULE TYPE:peptide (ix) FEATURE:
             (D) OTHER INFORMATION: Position 1 is Norleucine; position
                 3 is 4-Thiazoylalanine; position 4 is D-Naphthylalanine;
                 peptide is cyclic between positions 2 and 7

(xi) SEQUENCE DESCRIPTION: SEQ ID NO:4:

Xaa Asp Xaa Xaa Arg Trp Lys
                5

(2) INFORMATION FOR SEQ ID NO:5:

(i) SEQUENCE CHARACTERISTICS:
            (A) LENGTH: 7 amino acids
            (B) TYPE:amino acid
            (C) STRANDEDNESS:single
            (D) TOPOLOGY:cyclic (ii) MOLECULE TYPE:peptide (ix) FEATURE:
             (D) OTHER INFORMATION: Position 1 is Norleucine; position
                 3 is 1-Me Histidine; position 4 is D-Naphthylalanine;
                 position 6 is naphthylalanine; peptide is cyclic between
                 positins 2 and 7

(xi) SEQUENCE DESCRIPTION: SEQ ID NO:5:

Xaa Asp Xaa Xaa Arg Xaa Lys
                5

(2) INFORMATION FOR SEQ ID NO:6:

(i) SEQUENCE CHARACTERISTICS:
            (A) LENGTH: 7 amino acids
            (B) TYPE:amino acid
            (C) STRANDEDNESS:single
            (D) TOPOLOGY:cyclic (ii) MOLECULE TYPE:peptide (ix) FEATURE:
             (D) OTHER INFORMATION: Position 1 is Norleucine; position
                 3 is 3-Me Histidine; position 4 is D-Naphthylalanine;
                 position 6 is naphthylalanine; peptide is cyclic between
                 positions 2 and 7

(xi) SEQUENCE DESCRIPTION: SEQ ID NO:6:

Xaa Asp Xaa Xaa Arg Xaa Lys
                5

(2) INFORMATION FOR SEQ ID NO:7:

(i) SEQUENCE CHARACTERISTICS:
            (A) LENGTH: 7 amino acids
            (B) TYPE:amino acid
            (C) STRANDEDNESS:single
            (D) TOPOLOGY:cyclic (ii) MOLECULE TYPE:peptide (ix) FEATURE:
             (D) OTHER INFORMATION: Position 1 is Norleucine; position
                 3 is 4-Thiazoylalanine; position 4 is D-Naphthylalanine;
                 position 6 is naphthylalanine; peptide is cyclic between
                 positions 2 and 7

(xi) SEQUENCE DESCRIPTION: SEQ ID NO:7:

Xaa Asp Xaa Xaa Arg Xaa Lys
                5

-continued (2) INFORMATION FOR SEQ ID NO:8:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION: Position 1 is Norleucine; position
            4 is (2R,3R)-a-Me-Naphthylalanine; peptide is cyclic
            between positions 2 and 7

(xi) SEQUENCE DESCRIPTION: SEQ ID NO:8:

Xaa Asp His Xaa Arg Trp Lys
              5

(2) INFORMATION FOR SEQ ID NO:9:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION: Position 1 is Norleucine; position
            4 is (2R,3S)-a-Me-Naphthylalanine; peptide is cyclic
            between positions 2 and 7

(xi) SEQUENCE DESCRIPTION: SEQ ID NO:9:

Xaa Asp His Xaa Arg Trp Lys
              5

(2) INFORMATION FOR SEQ ID NO:10:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION: Position 1 is Norleucine; position
            4 is D-Phenylalanine; position 6 is L-naphthylalanine;
            peptide is cyclic between positions 2 and 7

(xi) SEQUENCE DESCRIPTION: SEQ ID NO:10:

Xaa Asp Trp Xaa Arg Xaa Lys
              5

(2) INFORMATION FOR SEQ ID NO:11:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION: Position 1 is Norleucine; position
            4 is D-Naphthylalanine; position 6 is L-naphthylalanine;
            peptide is cyclic between positions 2 and 7

(xi) SEQUENCE DESCRIPTION: SEQ ID NO:11:

Xaa Asp His Xaa Arg Xaa Lys
            5

(2) INFORMATION FOR SEQ ID NO:12:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION:  Position 1 is Norleucine; position
            4 is Naphthylalanine; peptide is cyclic between positions
            2 and 7

(xi) SEQUENCE DESCRIPTION: SEQ ID NO:12:

Xaa Asp His Xaa Arg Trp Lys
            5

(2) INFORMATION FOR SEQ ID NO:13:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION:  Position 1 is Norleucine; position
            4 is D-Naphthylalanine; position 5 is Norleucine; peptide
            is cyclic between positions 2 and 7

(xi) SEQUENCE DESCRIPTION: SEQ ID NO:13:

Xaa Asp His Xaa Xaa Trp Lys
            5

(2) INFORMATION FOR SEQ ID NO:14:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION:  Position 1 is Norleucine; position
            4 is D-Naphthylalanine; position 5 is Norleucine; peptide
            is cyclic between positions 2 and 7

(xi) SEQUENCE DESCRIPTION: SEQ ID NO:14:

Xaa Asp Trp Xaa Xaa Trp Lys
            5

(2) INFORMATION FOR SEQ ID NO:15:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:

(D) OTHER INFORMATION: Position 1 is Norleucine; position
            4 is D-phenylalanine; position 5 is Norleucine; peptide
            is cyclic between positions 2 and 7

(xi) SEQUENCE DESCRIPTION: SEQ ID NO:15:

Xaa Asp His Xaa Xaa Trp Lys
                  5

(2) INFORMATION FOR SEQ ID NO:16:

(i) SEQUENCE CHARACTERISTICS:
        (A) LENGTH: 7 amino acids
        (B) TYPE:amino acid
        (C) STRANDEDNESS:single
        (D) TOPOLOGY:cyclic (ii) MOLECULE TYPE:peptide (ix) FEATURE:
        (D) OTHER INFORMATION: Position 1 is Norleucine; position
            4 is D-Naphthylalanine; position 6 is D-naphthylalanine;
            peptide is cyclic between positions 2 and 7

(xi) SEQUENCE DESCRIPTION: SEQ ID NO:16:

Xaa Asp His Xaa Arg Xaa Lys